United States Patent [19]

Williams, III et al.

[11] 4,102,905

[45] Jul. 25, 1978

[54] AROMATIC DISULFONE DIANHYDRIDES

[75] Inventors: Frank J. Williams, III, Scotia; Paul E. Donahue, Schenectady, both of N.Y.

[73] Assignee: General Electric Company, Schenectady, N.Y.

[21] Appl. No.: 830,113

[22] Filed: Sep. 2, 1977

[51] Int. Cl.$^2$ ............................................ C07D 307/89
[52] U.S. Cl. .................................................. 260/346.3
[58] Field of Search ...................................... 260/346.3

[56] References Cited

U.S. PATENT DOCUMENTS

| 3,850,964 | 11/1974 | Williams | 260/346.3 X |
| 3,933,862 | 1/1976 | Williams | 260/346.3 |

*Primary Examiner*—Richard L. Raymond
*Attorney, Agent, or Firm*—Joseph T. Cohen; Charles T. Watts; Marvin Snyder

[57] ABSTRACT

There are provided bis(sulfone) aromatic dianhydrides and methods for making these materials. These aromatic disulfone dianhydrides can be used to make polyimides and polyesters, and can be used as curing agents for epoxy resins.

4 Claims, No Drawings

AROMATIC DISULFONE DIANHYDRIDES

The present invention relates to aromatic disulfone dianhydrides useful as intermediates for making polyimides and to methods for making such dianhydrides.

The bis(sulfone) aromatic dianhydrides of the present invention (hereinafter referred to as the "disulfones") are shown by the following formula,

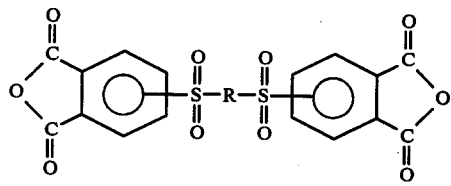

I where R is a divalent aromatic radical having from 6–30 carbon atoms.

Included by the disulfones of formula I are compounds of the formulas,

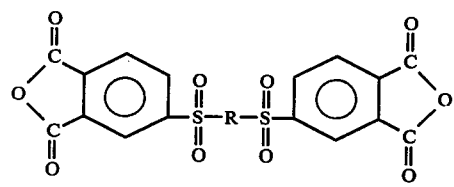

II

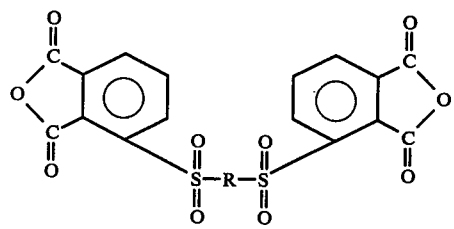

III

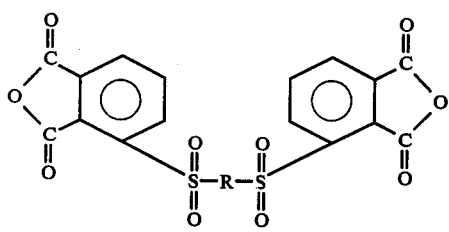

IV where R is as previously defined. Radicals included by R in formulas I–IV are, for example,

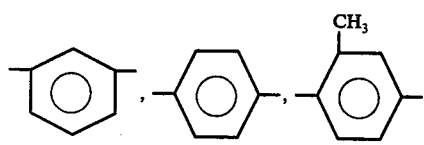

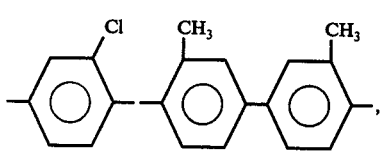

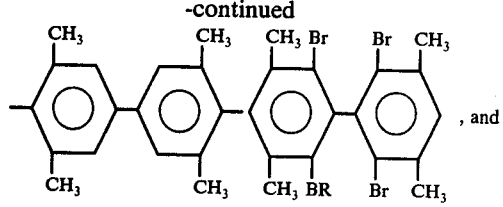

, and

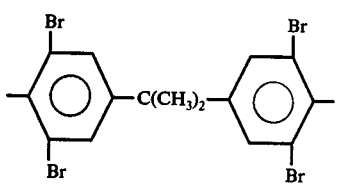

and divalent organic radicals of the general formula

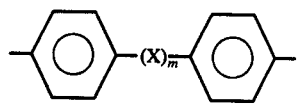

where X is a member selected from the class consisting of divalent radicals of the formulas, $-C_yH_{2y}-$,

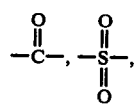

$-O-$, and $-S-$, where $m$ is 0 or 1, and $y$ is a whole number from 1 to 5.

Included among the disulfones of formula I are compounds such as 2,2-bis[4-(3,4-dicarboxy-phenylsulfonyl) phenyl] propane dianhydride, 2,4-bis[3,4-dicarboxy-phenylsulfonyl] chlorobenzene dianhydride, 4,4'-bis[3,4-dicarboxy-phenylsulfonyl] diphenylether dianhydride, 2,2-bis[4-(2,3-dicarboxy-phenylsulfonyl)phenyl] propane dianhydride, 2,4-bis[2,3-dicarboxy-phenylsulfonyl] chlorobenzene dianhydride, 4,4'-bis[2,3-dicarboxy-phenylsulfonyl] diphenylether dianhydride, 4,4'-bis[2,3-dicarboxy-phenylsulfonyl] biphenyl dianhydride, 4,4'-bis[2,3-dicarboxy-phenylsulfonyl]diphenylmethane dianhydride, 1,3-bis[3,4-dicarboxy-phenylsulfonyl] benzene dianhydride, 4,4'-[2,3-dicarboxy-phenylsulfonyl] [3,4-dicarboxy-phenylsulfonyl] diphenylether dianhydride, the compound having the formula

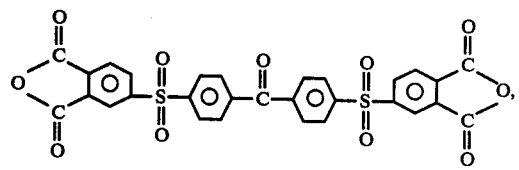

etc.

One method for making disulfones of formula I is preparing a dithiodianhydride of the formula

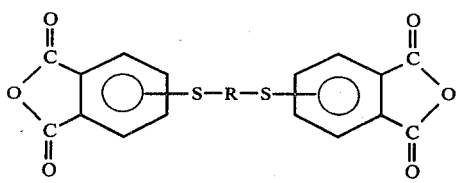

by effecting reaction in the presence of base between an aromatic dithiol of the formula,

HSRSH, and a substituted anhydride of the formula

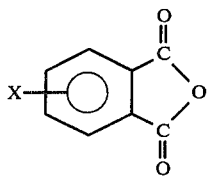

where R is as previously defined, and X is a radical selected from nitro, chloro, fluoro, bromo, etc. Other methods for making the dithio compound of formula V and further examples thereof are found in U.S. Pat. No. 3,933,862 issued Jan. 20, 1976 and assigned to the same assignee as the present invention. By reference, this patent is incorporated as part of the disclosures of the instant application.

After having prepared the dithio compound of formula V, the latter is then treated with a suitable oxidizing agent to first yield the tetraacid of the formula

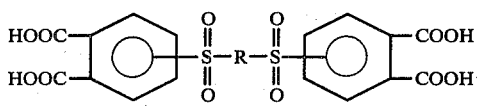

where R has the meaning above, which upon dehydration will yield the desired disulfone dianhydride of formula I. Any of a number of oxidizing agents may be employed to convert the dithio compound of formula V to the disulfone dianhydride. Among such oxidizing agents may be mentioned, for instance, hydrogen peroxide (for instance, in an acetic acid solution), potassium dichromate, peracids, nitric acid, sodium hypochlorite, potassium permanganate, etc. Oxidation reactions, particularly oxidation of sulfur atoms, are well known in the art and will be clearly apparent to persons skilled in such reactions how they can be advantageously carried out.

The oxidation of the dithio compounds of formula V yields the tetraacid of formula VI. The latter can be dehydrated by heating at elevated temperatures in the presence of a dehydrating agent such as acetic anhydride, to yield the desired dianhydride.

In carrying out the oxidation reaction, at least two equivalents of the oxidizing agent should be used per equivalent of dithio compound of formula V. Solvents, such as sulfuric acid, pyridine, acetic acid, etc., accompanied by the presence of water, can be used advantageously in the oxidation reaction. Generally the oxidation reaction proceeds relatively easily at room temperatures, although somewhat elevated temperature may be employed, keeping in mind that control of the oxidation reaction is better performed at lower temperatures.

The conversion of the tetraacid of formula VI to the dianhydride is advantageously carried out either by heat alone or by the use of a dehydrating agent such as acetic anhydride or DCC (dicyclohexylcarbodiimide) dissolved in a suitable inert solvent such as benzene or toluene. At least 1 mol of the dehydrating agent should be used per mol of water, which is expected to be removed by dehydrating the adjacent carboxy groups to form the dianhydride linkage. In the dehydration step, heat is advantageously employed and temperature of the order of about 75° to 250° C. can be used for times ranging from 1 hour to as much as 15-25 hours, depending on the compound being dehydrated, the dehydrating agent used, the speed within which it is desired to effect the dehydration, etc.

Thereafter, the dianhydride can be isolated by usual means, generally by merely filtering the reaction product subsequent to the dehydration step to yield the disulfone dianhydride in especially good yields.

In order that those skilled in the art may better understand how the present invention may be practiced, the following examples are given by way of illustration and not by way of limitation. All parts are by weight unless otherwise indicated.

EXAMPLE 1

A mixture of 3.0 parts 4,4'-diphenylether dithiol, 4.68 parts of 4-chlorophthalic anhydride, 2.85 parts triethylamine, and 38 parts anhydrous dimethyl formamide was stirred at 50° C. under a nitrogen atmosphere for 3 hours. The resulting mixture was cooled to room temperature and then slowly added to 200 parts 1.2 normal HCl. The precipitate thereby obtained was collected by filtration, dried, and then recrystallized from a toluene/acetic anhydride mixture to yield the dianhydride of the formula

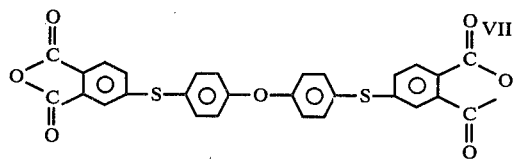

having a melting point 186.5°-188.5° C.

EXAMPLE 2

Using the dianhydride described in Example 1 (formula VII), 16.77 grams potassium dichromate was dissolved in 170 ml of 96% sulfuric acid and 250 ml water. A mixture of 20 grams of the dianhydride of formula VII was stirred with 785 ml glacial acetic acid at room temperature and the dichromate solution was added dropwise to the mixture. The system was then stirred for 16 hours at room temperature (about 25°-30° C.) after which time the reaction mixture was added to a large excess of water (2.4 liters). The resulting precipitate was collected by filtration and dried to give 16.25 grams (about 68% yield) of the tetraacid having the formula

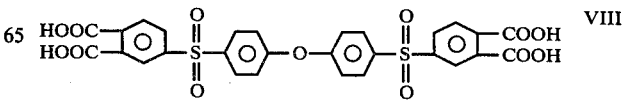

A 15.25 gram portion of the tetraacid was stirred at reflux for about 15 hours with 75 ml of toluene and 6.1 ml of acetic anhydride under a nitrogen atmosphere. The mixture was then cooled to room temperature and filtered to give 14.15 grams (98.5% yield) of the dianhydride having the formula

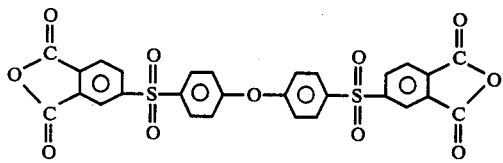

IX

Analysis of the product by infrared analysis established that the desired dianhydride had been obtained; the molecular weight was found to be 590 by mass spectral analysis (theoretical 590).

EXAMPLE 3

A mixture of 6.2 parts of 4-chlorophthalic anhydride, 3 parts of 4-chloro-m-benzene dithiol and 28 parts of anhydrous dimethyl formamide was stirred for 16 hours at room temperature under nitrogen atmosphere, to which was added 3.9 parts of triethylamine. Thereafter, 100 parts of 1.2 NHCl was added to give a precipitate which was collected and dried, and treated similarly as in Example 1 with an acetic acid/acetic anhydride mixture to give the dianhydride having the formula

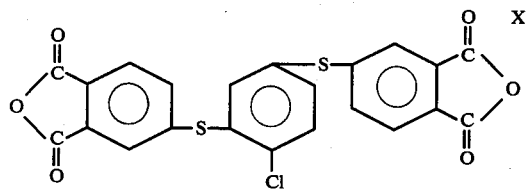

X

EXAMPLE 4

Using the dianhydride of formula X prepared in Example 3, 18.83 grams potassium dichromate was dissovled in 200 ml of 96% sulfuric acid and 280 ml water. A mixture of 20 grams of the dianhydride of formula X in 750 ml glacial acetic acid was stirred at room temperature while the dichromate solution was added dropwise. The solution was then stirred for 16 hours at room temperature and thereafter added to 2.5 liters of water. The homogeneous solution thus obtained was extracted with diethyl ether to give upon removal of the ether, 15.23 grams (63% yield) of the disulfone tetraacid having the formula

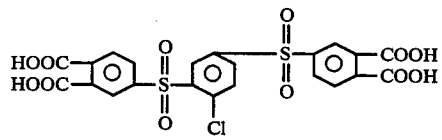

XI 14.23 grams of this latter tetraacid was stirred for 16 hours at the reflux temperature of the mass with 6.8 ml of acetic anhydride and 75 ml toluene. The solution was cooled and filtered to give 8.8 grams (66% yield) of the dianhydride of the formula

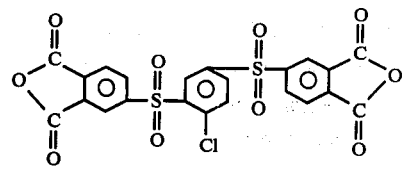

XII having melting point of 260°–263° C. Analysis by mass spectrometer (found molecular weight 533) and infrared established the identity of the compound to be the one shown in formula XII above.

EXAMPLE 5

The disulfone dianhydride of the formula

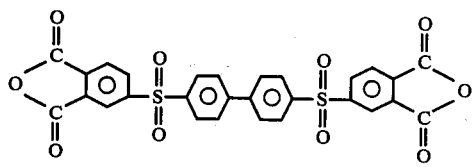

XIII can be prepared similarly as in Examples 1–4 by first making the corresponding dithiodianhydride as shown in Example 10 of U.S. Pat. No. 3,933,862, and oxidizing it and dehydrating the oxidized product in the manner described in Examples 1 to 4.

EXAMPLE 6

The disulfone dianhydride having the formula

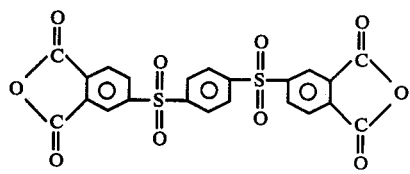

XIV can be made similarly as in Examples 1 to 4 by first preparing the corresponding dithiodianhydride, oxidizing it to the tetraacid disulfone, and subsequently dehydrating the tetraacid to the above-described dianhydride of formula XIV.

Additional examples and procedures for making the precursor dithiodianhydride compounds may be found described in the aforementioned patent of Frank J. Williams, U.S. Pat. No. 3,933,862, issued Jan. 20, 1976. Thereafter the dianhydride of the dithio compound can be oxidized in the manner described in Examples 2 and 4 above to give the desired disulfone tetraacid which in turn can be dehydrated to give the sought disulfone dianhydride.

It will of course be apparent to those skilled in the art that in addition to the starting materials and intermediate compositions which have been employed in the foregoing examples, other dithiodianhydrides can be oxidized to the corresponding tetraacid and then dehydrated to the desired dianhydride of formula I without departing from the scope of the invention. Many examples of such starting dithiodianhydride compounds may be found described in the aforesaid U.S. Pat. No. 3,933,862.

The disulfone dianhydrides of the present invention can be employed as epoxy curing catalysts. For example, a mixture of the disulfone dianhydride of Example 2 with an epoxy resin (derived from the reaction of 4,4'-isopropylidenediphenol and epichlorohydrin) can be heated at 150° to 250° C. to effect essentially complete cure of the epoxy resin. In addition, these disulfone dianhydrides can be used to make polyimide resins in the manner described in the accompanying patent application Ser. No. 830,114 of Williams and Donahue filed concurrently herewith and assigned to the same assignee as the present invention. Such polyimides can be blended with various fillers such as silica, glass fibres, etc. and molded at elevated temperatures to form molded products useful as heat-resistant plastics for applications such as motor grids, slot liners in motors, etc. Solutions of the polyimides can also be employed as insulation for electrical conductors.

What we claim as new and desire to secure by Letters Patent of the United States is:

1. A disulfone dianhydride having the general formula

where R is a radical selected from the class consisting of

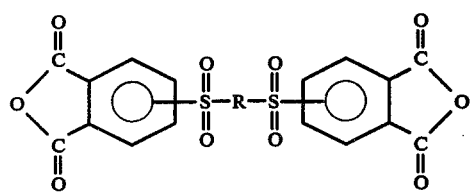

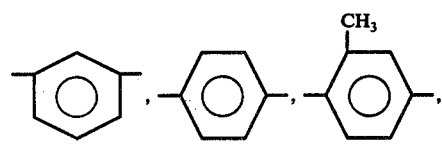

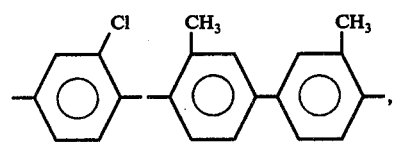

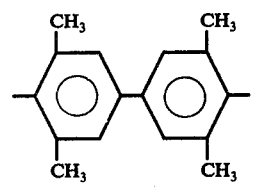

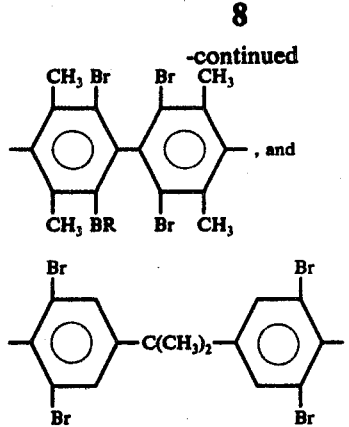

and divalent organic radicals of the general formula

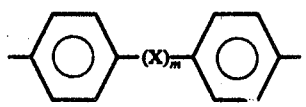

where X is a member selected from the class consisting of divalent radicals of the formulas, $-C_yH_{2y}-$, $$-\overset{O}{\underset{\parallel}{C}}-, \quad -\overset{O}{\underset{\parallel}{S}}-,$$

$-O-$, and $-S-$, where $m$ is 0 or 1, $y$ is a whole number from 1 to 5.

2. The disulfone dianhydride having the formula

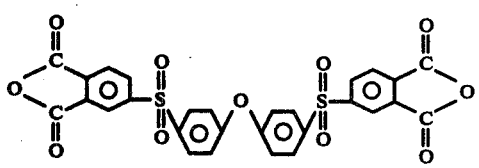

3. The disulfone dianhydride having the formula

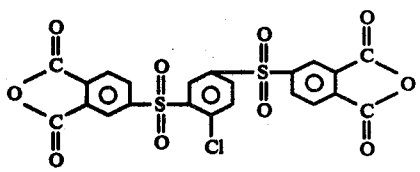

4. The disulfone dianhydride having the formula

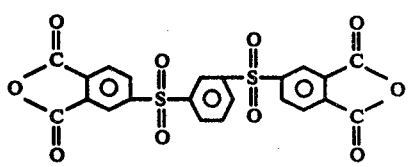

* * * * *